United States Patent [19]

Huang et al.

[11] Patent Number: 4,920,131

[45] Date of Patent: * Apr. 24, 1990

[54] QUINOLINE DERIVATIVES AND USE THEREOF AS ANTAGONISTS OF LEUKOTRIENE D$_4$

[75] Inventors: Fu-Chi Huang, Gwynedd; Robert A. Galemmo, Jr., Ambler; Henry F. Campbell, North Wales, all of Pa.

[73] Assignee: Rorer Pharmaceutical Corp., Ft. Washington, Pa.

[*] Notice: The portion of the term of this patent subsequent to Apr. 24, 2004 has been disclaimed.

[21] Appl. No.: 209,428

[22] Filed: Jun. 21, 1988

Related U.S. Application Data

[63] Continuation-in-part of Ser. No. 116,420, Nov. 3, 1987, and a continuation-in-part of Ser. No. 116,428, Nov. 3, 1987, and a continuation-in-part of Ser. No. 116,597, Nov. 2, 1987.

[51] Int. Cl.$^5$ ............... C07D 215/12; C07D 215/14; C07D 403/02; A61K 31/47
[52] U.S. Cl. ........................ 514/311; 514/314; 546/172; 546/174; 546/176; 546/153; 546/156; 546/177; 546/178; 546/180
[58] Field of Search ............... 546/176, 174, 153, 156, 546/172, 175, 177, 178, 155, 171, 179; 514/311, 314

*Primary Examiner*—David B. Springer
*Attorney, Agent, or Firm*—James A. Nicholson; Martin Savitzky; Imre Jim Balogh

[57] ABSTRACT

This invention relates to quinolinyl compounds of the general formula:

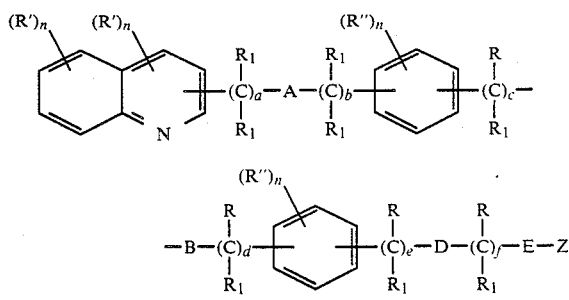

and the use of these compounds as pharmacological agents which are lipoxygenase inhibitors and/or leukotriene antagonists possessing anti-inflammatory and anti-allergic properties and their pharmaceutical compositions and processes for this preparation.

19 Claims, No Drawings

QUINOLINE DERIVATIVES AND USE THEREOF AS ANTAGONISTS OF LEUKOTRIENE D4

This application is a continuation-in-part application of copending U.S. patent applications Ser. No. 116,420, filed Nov. 3, 1987; Ser. No. 116,428, filed Nov. 3, 1987 and Ser. No. 116,597, filed Nov. 2 1987.

FIELD OF INVENTION

This invention relates to certain chemical compounds and their use as valuable pharmaceutical agents, particularly as lipoxygenase inhibitors and/or leukotriene antagonists possessing anti-inflammatory and anti-allergic properties.

SUMMARY OF THE INVENTION

This invention relates to the compounds described by the general Formula I and to therapeutic compositions comprising as active ingredient a compound of Formula I:

$$\text{Formula I}$$

where:
A is O or S;
B is a chemical bond, O, S, SO, $SO_2$, $NR_1$, $$-\overset{O}{\underset{\|}{C}}-,\quad -\overset{R_1}{\underset{|}{N}}-\overset{O}{\underset{\|}{C}}-,\quad -\overset{O}{\underset{\|}{C}}-\overset{R_1}{\underset{|}{N}}-\quad \text{or}\quad -\overset{R_1}{\underset{|}{C}}=\overset{R_1}{\underset{|}{C}}-$$

D is O, S, $NR_1$, $$-\overset{R_1}{\underset{|}{C}}=\overset{R_1}{\underset{|}{C}}-$$

or a chemical bond;
E is a chemical bond or $$-\overset{R_1}{\underset{|}{C}}=\overset{R_1}{\underset{|}{C}}-;$$

a is 0-2;
b is 0-1;
c is 0-4;
d is 0-5;
e is 0-4;
f is 0-5;
n is 0-2;
R' is independently hydrogen, alkyl, hydroxy, alkoxy, carboxy, carbalkoxy, halo, nitro, haloalkyl, cyano or acyl;

R" is independently hydrogen, hydroxy, alkoxy, halo, haloalkyl, $-CH_2R$, $-CH_2-O-(CH_2)_x-X$ or R;
$R_1$ is independently hydrogen, alkyl or aralkyl;
R is $-(CH_2)_x-X$; $-O-(CH_2)_x-X$; (when not geminal to A or B when A or B is O); $-S-(CH_2)_x-X$; or $-NR_1-(CH_2)_x-X$; where x is 0-3 and
X is hydrogen, alkyl, alkenyl, cycloalkyl, aryl aralkyl, hydroxy, alkoxy, aralkoxy, amino, mono- and dialkylamino, aralkylamino, acylamino, $-CONR_1R_1$, $-COOR$, CN, tetrazolyl, or acylsulfonamido;
vicinal R groups together may be $(CH_2)_y$—where y is 1-4, thus forming a 3-6 membered ring;
geminal $R_1$ and $R_2$ groups may together form a spiro substituent, $-(CH_2)_z-$, where z is 2 to 5;
geminal $R_1$ or $R_1$ and $R_2$ groups may together form an alkylidenyl substituent, $$\overset{CHR_1:}{\underset{\|}{\phantom{C}}}$$

Z is $-COOR_1$;

$$-CN;\quad -\overset{O}{\underset{\|}{C}}NHSO_2R_3$$

where $R_3$ is hydrogen, alkyl, haloalkyl, phenyl or benzyl;

$$-\overset{O}{\underset{\|}{C}}N(R_1)_2;$$

$-OR_1$ or tetrazolyl or substituted tetrazolyl where the substituent may be alkyl, carboxyalkyl or carbalkoxyalkyl; and pharmaceutically acceptable salts thereof.

The compounds of Formula I contain at least three aromatic rings. For the purposes of this invention these may be designated as shown in Formula II. The substitution pattern of these rings along the chain with respect to each other is as follows.

$$\text{Formula II}$$

Ring I    Ring II    Ring III

The substitution pattern of the quinoline ring, that is Ring I, is preferably at the 2-position for extending the side chain. As this side chain progresses from the quinoline ring, the two phenyl rings, designated Ring II and Ring III may be substituted along the chain in the ortho, meta or para positions with respect to each other and Ring II may also be substituted in the ortho, meta and para positions in respect to the quinoline ring.

The preferred substitution pattern for Ring II is meta or para, that is:

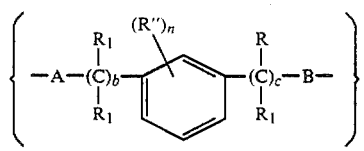    IIIa or

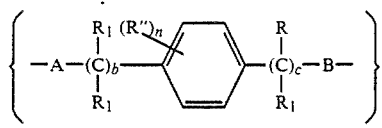    IIIb

Ring III however may be substituted equally in the ortho, metha or para positions, that is:

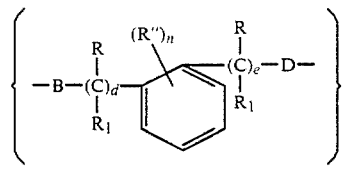    IVa

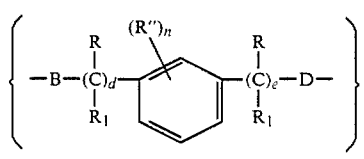    IVb or

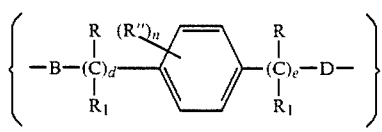    IVc

Further preferred compounds of this invention are described by Formula V below:

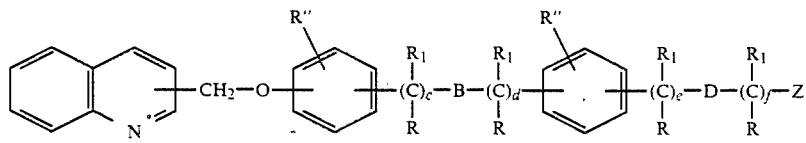    Formula V where one of R is —(CH$_2$)$_x$—X; —S—(CH$_2$)$_x$—X; —O—(CH$_2$)$_x$—X; (when not geminal to A or B when A or B is O); —NR$_1$—(CH$_2$)$_x$—X; and/or one of R" is —CH$_2$R; R or —CH$_2$—O—(CH$_2$)$_x$—X and X is —CONR$_1$R$_1$, —COOR$_1$, —CN, tetrazolyl or acylsulfonamido.

The more preferred compounds of Formula V are those where B is O, S,

or a chemical bond; Z is —COOR$_1$ —CON(R$_1$)$_2$ tetrazolyl and R and R" are as described above.

It is most preferred that the molecule contain what could be considered to be two side chains which are formed from R and/or R" moieties in combination with the —(C)$_e$—D—(C)$_f$—E—Z portion of the molecule or when e and f are both 0 and D and E are both chemical bonds then the two side chains are formed from any combination of R and R" moieties. It's still most preferred that these side chains contain acid and/or basic functions. This will become more evident as the invention is described in greater detail.

In addition, the present invention relates to the method of using these compounds as lipoxygenase inhibitors and/or leukotriene antagonists possessing anti-inflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl, etc.

"Alkoxy" refers to a loweralkyl—O—group.

"Alkenyl" refers to a hydrocarbon having at least one point of unsaturation and may be branched or straight chained. Preferred alkenyl groups have six or less carbon atoms present such as vinyl, allyl, ethynyl, isopropenyl, etc.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms such as cyclopropyl, cyclohexyl, etc.

"Acyl" means an organic radical derived from an organic acid by removal of its hydroxyl group. Preferred acyl groups are acetyl, propionyl, benzoyl, etc.

"Halo" means a halogen. Preferred halogens include, chloride, bromide and fluoride. The preferred haloalkyl group is trifluromethyl.

The compounds of this invention may be prepared in segments as is common to a long chain molecule. Thus it is convenient to synthesize these molecules by employing condensation reactions at the A, B and D cites of the molecule. For this reason the present compounds may be prepared by art recognized procedures from known compounds or readily preparable intermediates. Exemplary general procedures are as follows. Thus in order to prepare the compound

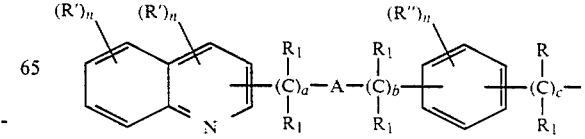

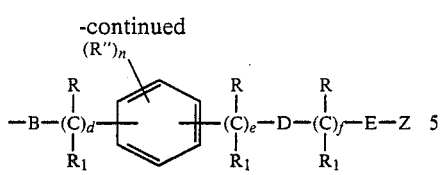

The following reactions or combinations of reactions may be employed.

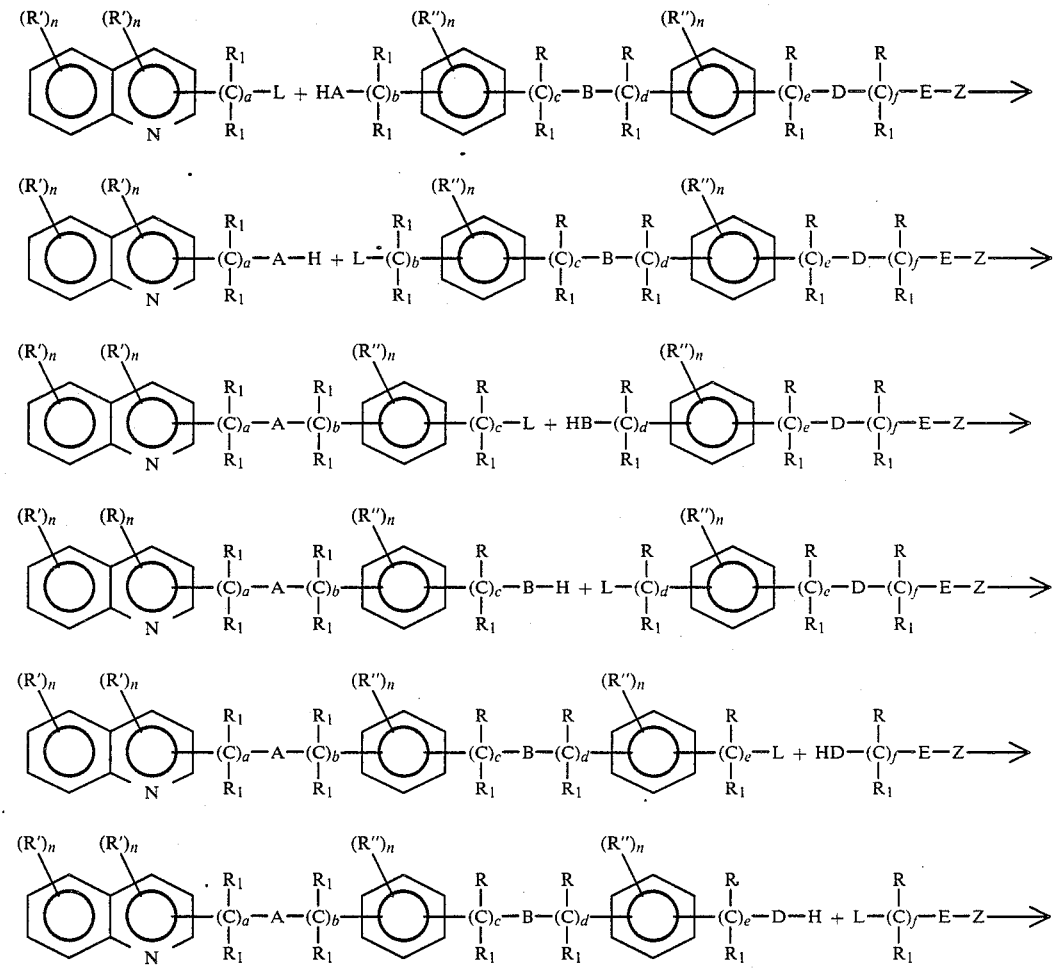

where:
R, R', R", R, a, b, c, d, e, f, n, A, and D are as defined above; B is O or S; E is a chemical bond; Z is

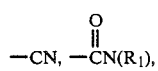

—COOR$_1$ or tetrazolyl, and L is a leaving group, such as halo, tosylate, or mesylate. Where B is O or S, any base normally employed to deprotonate an alcohol or thiol may be used, such as sodium hydride, sodium hydroxide, triethyl amine, sodium bicarbonate or diisopropyl/ethylamine.

Reaction temperatures are in the range of room temperature to reflux and reaction times vary from 2 to 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where B is SO or SO$_2$ then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating with 30% H$_2$O$_2$.

Those compounds where B is

may be prepared by the following reaction sequence:

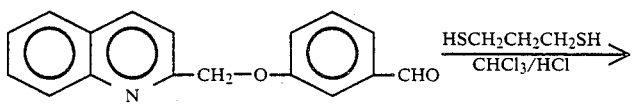

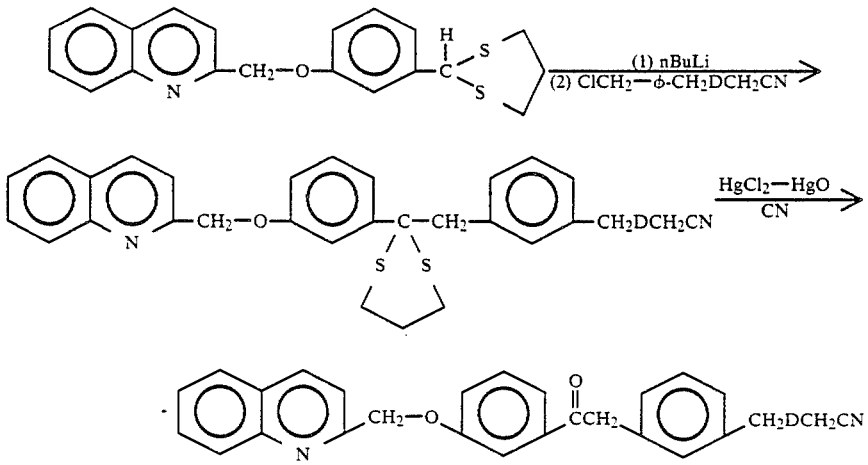

Condensation of the aldehyde with 1,3-propanedithiol results in the dithiane compound. This may be carried out in chloroform at reduced temperatures (−20° C.) while bubbling HCl gas into the reaction mixture. The dithiane compound is then treated with N-butyllithium in nonpolar solvent at −78° C. and then reacted with the substituted benzyl chloride. This results in addition of the Ring III to the molecule. The dithiane moiety is then treated with a mercuric chloride-mercuric oxide mixture to form the complex which is then split off leaving the desired compound.

Wittig condensation also may take place at the B position of the molecule of Formula I as follows:

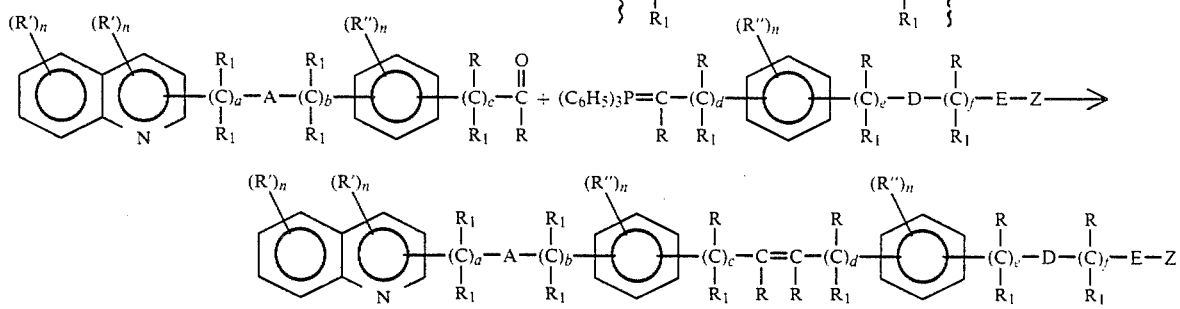

This may be carried out using normal Witting reaction conditions. When the appropriate aldehyde or ketone is reacted with a Wittig reagent then condensation results in formation of the double bond. This may then be reduced catalytically by known procedures such as Pd/C or any other suitable hydrogenating condition.

The Wittig reagent is prepared by known art recognized procedures such as reaction of triphenyl phosphine or diethylphosphone, with a substituted alkyl bromide followed by treatment with a strong organometallic or alkoxide base such as n-BuLi or NaOH results in the desired ylide.

Of course this Wittig condensation may also take place when the Wittig reagent is formed on Ring II position of the molecule which is then condensed with the aldehyde from the Ring III portion.

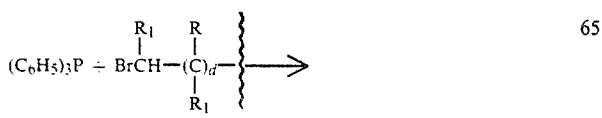

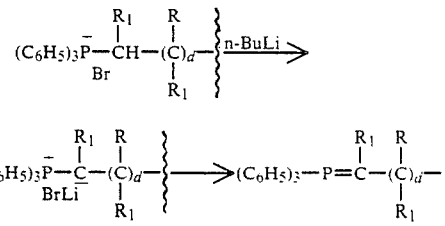

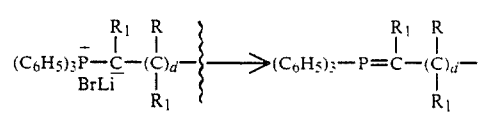

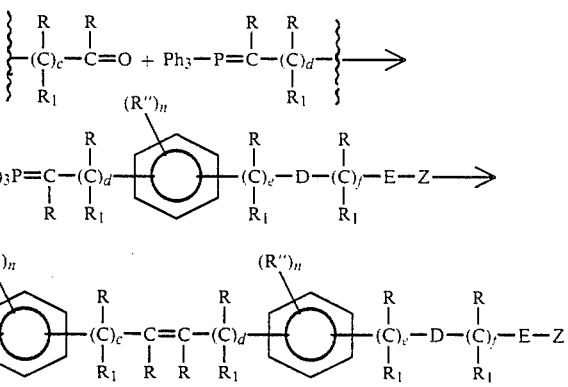

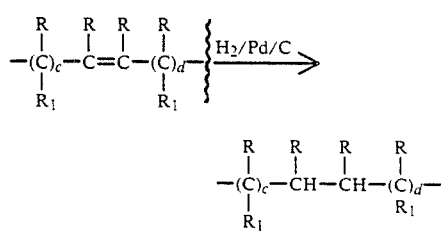

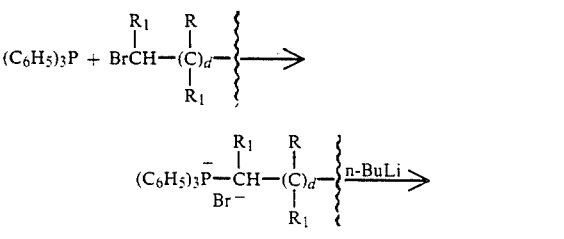

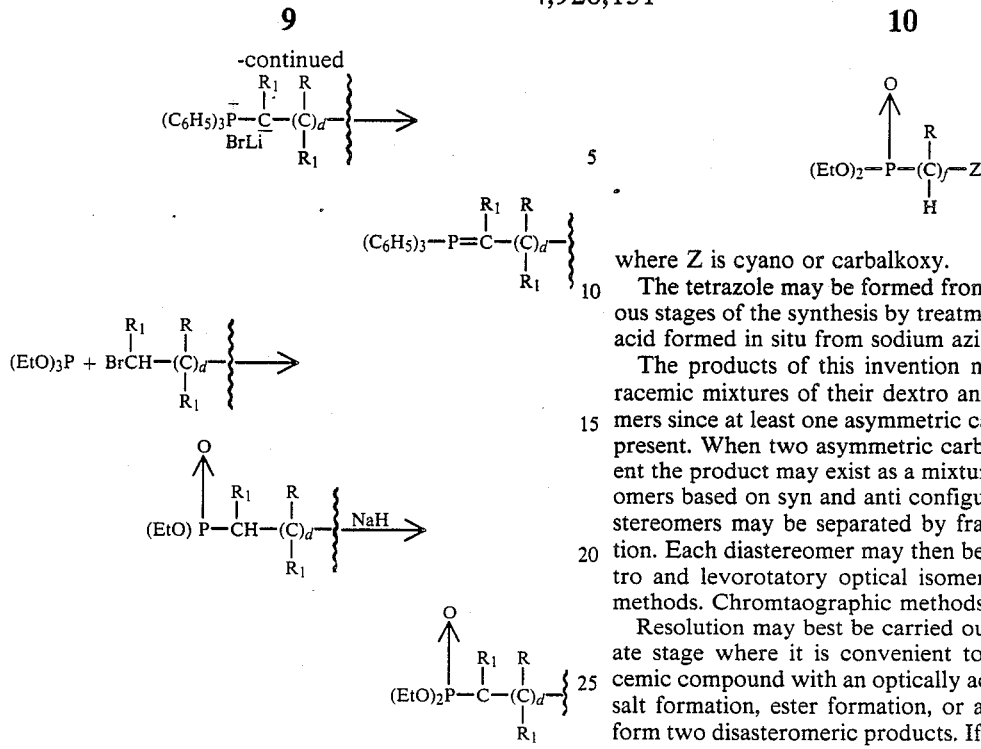

When B is

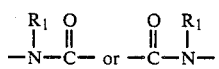

then condensation of the acid halide with the appropraite aniline will give the desired compound

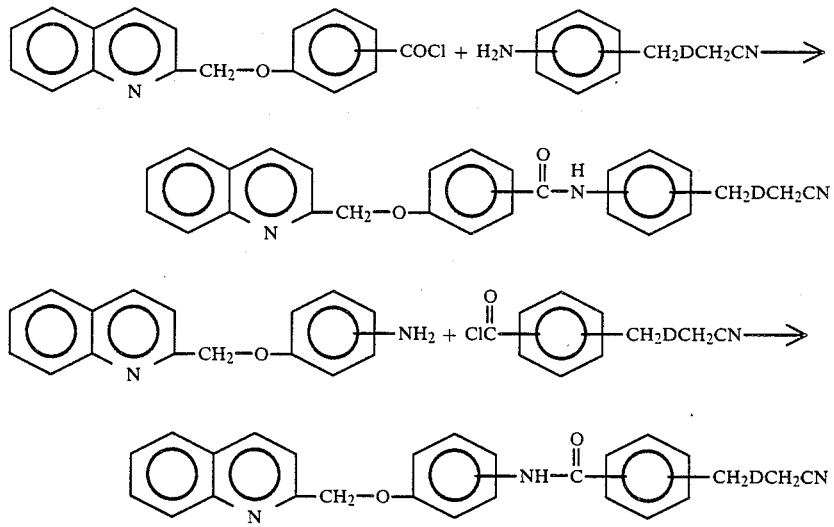

Those compounds where D and/or E are $$-\underset{R_1}{\overset{R_1}{C}}=\underset{}{\overset{}{C}}-$$

are prepared by reacting the appropriate aldehyde and ketone with a substituted Wittig reagent of the formula $$(EtO)_2-\overset{O}{\overset{\uparrow}{P}}-\underset{H}{\overset{R}{(C)_f}}-Z$$

where Z is cyano or carbalkoxy.

The tetrazole may be formed from the nitrile at various stages of the synthesis by treatment with hydrazoic acid formed in situ from sodium azide and an acid.

The products of this invention may be obtained as racemic mixtures of their dextro and levorotatory isomers since at least one asymmetric carbon atom may be present. When two asymmetric carbon atoms are present the product may exist as a mixture of two disastereomers based on syn and anti configurations. These diastereomers may be separated by fractional crystallization. Each diastereomer may then be resolved into dextro and levorotatory optical isomers by conventional methods. Chromtaographic methods may also be used.

Resolution may best be carried out in the intermediate stage where it is convenient to combine the reacemic compound with an optically active compound by salt formation, ester formation, or amide formation to form two disasteromeric products. If an acid is added to an optically active base, then two disasteromeric salts are produced which posses different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of may of these possible groups may be found in "Protective Groups in Organic Synthesis" by T. W. Green, John Wiley and Sons, 1981. For example, nitro groups can be added to the aromatic ring by nitration and the nitro groups converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention have potent activity as leukotriene antagonists and as such possess therapeutic value in the treatment of inflammatory conditions and allergic responses such as anaphlaxis and asthma.

Protocol for SRS-A (slow reacting substance of anaphylaxis) Antagonists

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure-(Proc. Nat'l. Acad. Sci., U.S.A. Volume 77, pp. 4354–4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen-5% carbon dioxide and maintained at 37° C. The assay buffer has been made as follows: for each liter of buffer the following are added to approximately 800 ml of water distilled in glass-6.87 g NaCl, 0.4 g $MgSO_4.7H_2O$), and 2.0 g D-glucose. Then a solution of 0.368 g $CaCl_2.H_2O$ in 100 ml glass-distilled water is slowly added to the buffer. Sufficient water is added to adjust the volume to 1 liter, and the solutin is aerated with 95% oxygen-5% carbon dioxide. Usually 10 liters of buffer are used for an experiment with 4 tissues. After the tissues have been repeatedly washed and allowed to equilibrate in the tissue bath, they are challenged with 1 M histamine. After maxium contractions have been obtained, the tissues are washed, and allowed to relax back to baseline tension. This histamine challenge procedure is repeated at least 1 to 2 more times to obtain a repeatable control response. The average response to 1 M histamine for each tissue is used to normalize all other challenges.

Responses of each tissue to a predetermined concentration of leukotriene are then obtained. Usually test compounds are examined initially at 30 M on resting tension of the tissues without any added agonist or antagonist to determine if the compound has any possible intrinsic activity. The tissues are washed and the test compound is added again. Leukotriene is added after the desired preincubation time. The intrinsic activity of the compounds, and their effect on leikotriene-induced contractions are then recorded.

The results of this test for the compounds of the this invention indicates that these compounds are considered to be useful leukotriene antagonists.

Inhibitions of ($^3$H)-$LTD_4$ Binding Membranes from Guinea Pig Lung.

A. Preparation of the Crude Receptor Fraction

This procedure was adapted from Mong et al. 1984). Male guinea pigs are sacrificed by decapitation and their lungs are quickly removed and placed in a beaker containing ice-cold homogenization buffer. The lungs are separated from connective tissue, minced with scissors, blotted dry and weighed. The tissue is then homogenized in 40 volumes (w/v) of homogenization buffer with a Polytron at a setting of 6 for 30 seconds. The homogenate is centrifuged at $1000 \times g$ for 10 minutes (e.g. 3500 RPM, SS-34 Rotor). The supernate is filtered through two layers of cheese cloth and centrifuged at $30,000 \times g$ for 30 minutes (e.g. 18,500 RPM SS-34 Rotor), after which the resulting pellet is resuspended in 20 volumes of assay buffer by hand homogenization using a Dounce homogenizer. The final pellet is resuspended in 10 volumes of assay buffer and kept at 4° C. until use.

B. Binding Assay

Each assay tube ($16 \times 100$ mm) contains the following:
409 μL Assay Buffer
10 μL Test compound or solvent
100 μL $^3$H-$LTD_4$ (ca. 17,500 DMP)
400 μL Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to quilibrate for 4–6 hours, the readioactivity is counted with a liquid scintillation counter appropriately set for tritium.

The required control assay tubes include the following:
(a) Total Binding: No test compound is added; buffer is substituted.

(b) Non-specific Binding: Non-labeled ligand is added at a concentration of 1M.

(c) Solvent Controls: If test compound is dissolved in a solvent, controls for both Total Binding and Non-Specific Binding containing solvent but no compounds are required.

The results of this test indicate that the compounds for this invention exhibit valuable properties which are useful in the treatment of inflammatory conditions and allergic responses.

The compounds of the present invention can be administered to a mammalian host in a variety of forms adapted to the chosen route of administration, i.e., orally, or parenterally. Parental administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit·form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100M/day or from about 0.1 mg to about 50 mg/kg of body weight per day and higher although it may be administered in several different dosage units. Higher dosages are required for oral administration.

The compounds of the present invention may be prepared by the following representative examples.

EXAMPLE 1

(3-(quinolin-2-yl)methyloxy)phenol

A mixture of (0.06 mol) of 2-quinolinylmethyl chloride HCl, (0.06 mol) of 1,3-benzenediol and 18 g of potassium carbonate in 50 ml of DMF is heated at 70° C. overnight. The reaction mixture is poured into water, and the precipitated product is collected, filtered and dried to give (3-(quinolin-2-yl)methyloxy)phenol.

EXAMPLE 2

When 2-quinolinylmethyl chloride of Example 1 above is replaced by the quinoline compounds of Table I below then the corresponding product is obtained.

TABLE I 2-chloromethylquinoline
2-bromomethylquinoline
2-(1-chloroethyl)quinoline
2-(2-chloroethyl)quinoline
2-bromoethylquinoline
3-chloromethylquinoline
4-chloromethylquinoline
2-($\beta$-chloroethyl)quinoline
2-($\beta$-chloropropyl)quinoline
2-($\beta$-chloro-$\beta$-phenethyl)quinoline
2-chloromethyl-4-methylquinoline
2-chloromethyl-6-methylquinoline
2-chloromethyl-8-methylquinoline
2-chloromethyl-6-methoxyquinoline
2-chloromethyl-6-nitroquinoline
2-chloromethyl-6,8-dimethylquinoline
2-chloromethyl-7-chloroquinoline
2-chloromethyl-7-bromoquinoline
2-chloromethyl-7-nitroquinoline
2-chloromethyl-7-methylquinoline

EXAMPLE 3

When 1,3-benzenediol alcohol of Example 1 above is replaced by the compounds of Table II below then the corresponding product is obtained.

TABLE II 1,2-benzenediol
1,3-benzenediol
1,4-benzenediol
2-mercaptophenol
3-mercaptophenol
4-mercaptophenol
1,3-dimercaptobenzene
1,4-dimercaptobenzene
3-hydroxybenzyl alcohol
3-hydroxyethylphenol
4-hydroxybenzyl alcohol
4-hydroxyethylphenol
2-methylresorsinol
5-methylresorsinol
5-methoxyresorsinol
5-methyl-1,4-dihydroxybenzene
3-(N-acetylamino)phenol
3-(N-acetylamino)benzyl alcohol
2-hydroxy-$\alpha$-methylbenzyl alcohol
2-hydroxy-$\alpha$-ethylbenzyl alcohol
2-hydroxy-$\alpha$-propylbenzyl alcohol
3-hydroxy-$\alpha$-methylbenzyl alcohol
3-hydroxy-$\alpha$-ethylbenzyl alcohol
3-hydroxy-$\alpha$-propylbenzyl alcohol
4-hydroxy-$\alpha$-methylbenzyl alcohol
4-hydroxy-$\alpha$-ethylbenzyl alcohol
4-hydroxy-$\alpha$-propylbenzyl alcohol

EXAMPLE 4

When the compounds of Table I, Example 2 are reacted with the compounds of Table II, Example 3 under the conditions of Example 1 then corresponding products are obtained.

EXAMPLE 5

2-(2-(3-((quinolin-2-yl)methyloxy)phenoxymethyl)-phenoxy)propionic acid

A. ethyl 2-(2-Methylphenoxy)propionate

A mixture of 10.8 g (0.1 mol) of o-cresol, 18.1 g (0.1 mol) of ethyl 2-bromopropionate, and 14.5 g of $K_2CO_3$ in 50 ml of DMF is heated at 70° C. for 3 days. The reaction mixture is poured into $H_2O$, and extracted with ethyl acetate. The organic solution is dried and evaporated to give ethyl 2-(2-methylphenoxy)propionate which is used directly in the next step.

B. ethyl 2-(2-bromomethylphenoxy)proprionate

A mixture of 6 g (0.029 mol) of ester obtained from step A, 5.6 g (0.031 mol) of N-bromosuccinimide and 100 mg of benzoyl peroxide in 100 ml of $CCl_4$ is heated to reflux while irradiated with a sun-lamp, for 1 hour. The reaction mixture is cooled down and filtered to dryness to give ethyl 2-(2-bromomethylphenoxy)propionate which is used directly in the next step.

C. ethyl 2-(2-(3-((quinolin-2-yl)methyloxy)phenoxymethyl)-phenoxy)propionate To a solution of (5.23 mmol) of 3-(quinolin-2-yl)methyloxyphenol and (5.23 mmol) of the bromide from step B in 90 ml of 8:1—acetone:DMF is added 1.52 g (10.97 mmol, 2.1 equiv) of $K_2CO_3$. The mixture is refluxed overnight, then partitioned between EtOAc and $H_2O$. The organics are dried, filtered, and concentrated in vacuo. This is then purified by flash column chromatography to give ethyl 2-(2-(3-((quinolin-2-yl)methyloxy)phenoxymethyl)phenoxy)propionate which is used directly in the next step.

D. 2-(2-(3-((quinolin-2-yl)methyloxy)phenoxymethyl)-phenoxy)propionic acid

To a solution of (2.65 mmol) of the ester from step C in 25 ml of EtOH is added 10 ml (10.0 mmol, 3.75 equiv) of 1N NaOH. The mixture is stirred for 1 hour at room temperature which time the mixture is acidified to pH~4 using 1N HCl. A precipitate forms which is filtered off and recrystallized from hot MeOH-$Et_2O$ to afford 2-(2-(3-((quinolin-2-yl)methyloxy)phenoxymethyl)phenoxy)propionic acid.

When 3-((quinolin-2-yl)methyloxy)phenol of Step C above is replaced with 3-((quinolin-2-yl)methyloxy)-mercaptobenzene or 4-((quinolin-2-yl)methyloxy)-phenol, then the products prepared are 2-(2-(3-((quinolin-2-yl)methyloxy)phenylthiomethyl)phenoxy)propionic acid or 2-(2-(4-((quinolin-2-yl)methyloxy)-phenoxymethyl)phenoxy)propionic acid.

EXAMPLE 6

When the compounds prepared by Examples 2–4 are used in place of (3-(quinolin-2-yl)methyloxy)phenol in Example 5, then the corresponding product is prepared.

EXAMPLE 7

5-(2-(4-quinolin-2-yl)methyloxy)phenoxymethyl)benzyl)tetrazole

A.

2-(4-((quinolin-2-yl)methyloxy)phenoxymethyl)benzyl chloride

A solution of (10.11 mmol) of 4-((quinolin-2-yl)methyloxy)phenol, (30.33 mmol, 3 equiv.) of 2-chloromethylbenzyl chloride and 4.2 g (30.33 mmol, 3 equiv) of $K_2CO_3$ in 100 mL of 8:1—acetone:DMF is refluxed for 24 hrs. The mixture is poured into ice-water and allowed to stand for 1½ hours. The precipitate that forms is filtered off, redissolved in EtOAc, dried, and concentrated in vacuo. The crude product is filtered by flash column chromatography to afford 2-(4-((quinolin-2-yl)methyloxy)phenoxymethyl)benzyl chloride which is used directly in the next step.

B.

2-(4-((quinolin-2-yl)methyloxy)phenoxymethyl)benzylnitrile

A mixture of (4.9 mmol) of 2-(4-((quinolin-2-yl)methyloxy)phenoxymethyl)benzyl chloride (22.3 mmol, 2 equiv) of KCN, and 100 mg of adogen 464 phase transfer catalyst in 70 mL of toluene and 70 mL of $H_2O$ is refluxed for 24 hours. The reaction mixture is partitioned between EtOAc and $H_2O$. The organic layer is separated, dried and concentrated in vacuo to afford a precipitate which is recrystallized from $CH_2Cl_2$-pet to give 2-(4-((quinolin-2-yl)methyloxy)phenoxymethyl)benzylnitrile.

C.

5-(2-(4-(quinolin-2-yl)methyloxy)phenoxymethyl)benzyl)tetrazole

A solution of (3.19 mmol) of 2-(4-((quinolin-2-yl)methyloxy)phenoxymethyl)benzylnitrile (63.07 mmol, 20 equiv) of $NaN_3$, and 3.4 g (63.07 mmol, 20 equiv) of $NH_4Cl$ in 20 mL of DMF is heated at 110° C. for 5 days under inert atmosphere. The reaction mixture is poured into ice water and allowed to stand for 1 hour. The precipitate that forms is filtered off and redissolved in $CH_2Cl_2$. To this is added 1N NaOH and the sodium salt that forms is filtered off. The salt is redissolved into hot $H_2O$, then acidified to pH~4 using 1N HCl. The precipitate that forms is filtered off, triturated with hot MeOH, and filtered to afford 5-(2-(4-(quinolin-2-yl)methyloxy)phenoxymethyl)benzyl)tetrazole.

EXAMPLE 8

2-hydroxy-3-((2-carboxyethyl)thio)-3-[(2-(4-((quinolin-2-yl)methyloxy)phenoxymethyl)phenyl)]propionic acid

A. ethyl 2,3-oxido-3-(2-bromoethylphenyl)propionate

To a solution of 5 g (41.61 mmol) of o-tolualdehyde and 5.1 g (41.61 mmol) of ethyl-2-chloroacetate in 10 mL of EtOH at 0° C. is added dropwise a solution of 0.96 g (41.61 mmol) of Na in 40 mL of EtOH over a period of 15 minutes. The mixture is then stirred at room temp for 3 days. The reaction mixture is partitioned between $Et_2O$ and $H_2O$. The organics are dried and concentrated in vacuo to give 5.2 g of the crude epoxide as a yellow oil. This crude oil is redissolved in 100 mL of $CCl_4$ and to this is added 7.41 g (41.61 mmol) of NBS and 20 mg of benzoyl peroxide as a radical initiator. The reaction mixture is refluxed under a high intensity lamp for 1 h. The reaction is cooled to 0° C. and the precipitate filtered off. The filtrate is concentrated in vacuo to give a yellow oil which is purified by flash column chromatography to give ethyl 2,3-oxido-3-(2-bromoethylphenyl)propionate in the form of a yellow oil which is used directly in the next step.

B. ethyl 2,3-oxido-3-(2-(4-((quinolin-2-yl)methyloxy)phenoxymethyl)phenyl)propionate A mixture of 4-((quinolin-2-yl)methyloxy)phenol (0.01 mol), ethyl 2,3-oxido-3-(2-bromoethylphenyl)propionate, and 0.012 mol of $K_2CO_3$ in 50 mL of DMF is heated at 70° C. overnight. The reaction mixture is poured into $H_2O$, extracted with ethyl acetate. The organic layer is separated, dried and evaporated to dryness. Purification by flash chromatography gives ethyl 2,3-oxido-3-[2-(4-((quinolin-2-yl)methyloxy)phenoxymethyl)phenyl]propionate.

C.

2-hydroxy-3-((2-carboxyethyl)thio)-3-[(2-(4-((quinolin-2-yl)methyloxy)phenoxymethyl)phenyl)]propionic acid A solution of ethyl 2,3-oxido-3-(4-((quinolin-2-yl)methyloxy)phenoxymethyl)phenyl)propionate (5 mmol), ethyl mercaptopropionate (5 mmol); $Et_3N$ (5 mmol) in 15 mL of MeOH is stirred at room temperature for 3 days. The reaction mixture is treated with 5 mmol of sodium methoxide overnight and then poured into $H_2O$ and extracted with EtOAc. The organic solution is dried and evaporated to dryness, and the residue filtered by flash chromatography. The ester is then hydrolyzed with NaOH solution, acidified with 1N HCL solution, which after purification by flash chromatography gives 2-hydroxy-3-((2-carboxyethyl)thio)-3-[(2-(4-((quinolin-2-yl)methyloxy)phenoxymethyl)phenyl)]propionic acid.

EXAMPLE 9 ethyl 4-(2-(4-((quinolin-2-yl)methyloxy)phenoxymethyl)-phenoxy)-4-carbethoxybutyrate 4-(2-(4-((quinolin-2-yl)methyloxy)phenoxymethyl)-phenoxy)-4-carboxybutyric acid

A. ethyl 4-carbethoxy-4-(2-methylphenoxy)butyrate

A mixture of o-cresol (0.1 mol) and diethyl 2-bromoglutarate (0.1 mol) and $K_2CO_3$ (0.11 mol) in 50 mL of DMF are heated at 70° C. overnight. The reaction is poured into water and extracted with ethyl acetate. The organic solution is washed with water, 0.1N NaOH solution, dried and evaporated to give ethyl 4-carbethoxy-4-(2-methylphenoxy)butyrate which is used directly in the next step.

B. 2-(1,3-dicarbethoxypropoxy)benzyl bromide

A mixture of ethyl 4-carbethoxy-4-(2-methylphenoxy)butyrate (0.05 mol) and NBS (0.055 mol) and 150 mg of benzoyl peroxide in 150 mL of $CCl_4$ is refluxed and shined with a sun lamp for 2 hours. Filtration and evaporation of solvent gives 2-(1,3-dicarbethoxypropoxy)-benzyl bromide which is used without purification.

C. ethyl 4-(2-(4-((quinolin-2-yl)methyloxy)phenoxymethyl)phenoxy)-4-carbethoxybutyrate

4-(2-(4-((quinolin-2-yl)methyloxy)phenoxymethyl)phenoxy)-4-carboxybutyric acid A mixture of 4-((quinolin-2-yl)methyloxy)phenol (0.01 mol) and 0.011 mol of $K_2CO_3$ in 50 mL of DMF are heated at 70° C. overnight. The reaction mixture is poured into water followed by extraction with ethyl acetate. The organic solution is washed with water, dried and evaporated to dryness.

The crude product is purified by column chromatography to give ethyl 4-(2-(4-((quinolin-2-yl)methyloxy)phenoxymethyl)phenoxy)-4-carbethoxybutyrate. The ester is treated with 1N NaOH solution (30 mL) in dioxane overnight. The reaction mixture is then acidified, and purified by flash chromatography which gives 4-(2-(4-((quinolin-2-yl)methyloxy)phenoxymethyl)phenoxy)-4-carboxybutyric acid.

EXAMPLE 10

When the procedure of Example 9 is followed and diethyl 2-bromoglutonate is replaced by the compounds of Table III below, then the corresponding product is prepared.

Table III diethyl 2-bromomalonate
diethyl 2-bromosuccinate
diethyl 2-bromoglutarate
diethyl 3-bromoglutarate
diethyl 2-bromoadipate
diethyl 3-bromoadipate
ethyl 2-bromo-2-dimethylacetamidoacetate
ethyl 2-bromo-3-dimethylacetamidopropionate
ethyl 2-bromo-4-dimethylacetamidobutyrate
ethyl 2-bromo-5-dimethylacetamidovalerate
ethyl 3-bromo-4-dimlethylacetamidobutyrate
ethyl 2-bromo-5-dimethylacetamidovalerate
ethyl 3-bromo-5-dimethylacetamidovalerate
ethyl 4-bromo-5-dimethylacetamidovalerate

EXAMPLE 11

When the procedure of Example 3 is follwed and 2-bromopropionate is replaced by the compounds of Table IV below, then the corresponding product is obtained.

Table IV ethyl 2-bromoacetate
ethyl 2-bromopropionate
ethyl 2-bromobutyrate
ethyl 3-bromobutyrate
ethyl 2-bromovalerate
ethyl 2-bromo-3-methylvalerate
ethyl 3-bromovalerate
N,N-dimethyl-2-bromopropionamide
N,N-dimethyl-2-bromobutyramide
N,N-dimethyl-2-bromovaleramide
N,N-dimethyl-3-bromovaleramide

EXAMPLE 12

When the procedures of Example 5, 9, 10 and 11 are followed and o-cresol is replaced by the compounds of Table V below, then the corresponding product is prepared.

Table V o-cresol, m-cresol, p-cresol
o-mercaptotoluene, m-mercaptotoluene, p-mercaptotoluene,
3-hydroxy-4-carbethoxytoluene
3-hydroxy-4-dimethylcarbamyltoluene
3-hydroxy-4-dimethylcarbamylmethyltoluene
3-hydroxy-5-dimethylcarbamylmethoxytoluene
3-mercapto-4-carbethoxytoluene
3-mercapto-4-dimethylcarbamyltoluene
3-mercapto-4-dimethylcarbamylmethyltoluene
3-mercapto-5-dimethylcarbamylmethoxytoluene
methyl 4-methylsalicylate, methyl 3-methylsalicylate When the procedure of Example 5 is followed and o-cresol is replaced by 5-methylresorcinol, 4-methylresorcinol or methylhydroquinone, then the corresponding products are prepared.

EXAMPLE 13

2-(3-(2-(3-(2-quinolinylmethyloxy)phenyl)2-carboxyethylthio)ethyl)pehnoxy)acetic acid

A. ethyl 2-(3-(2-(3-hydroxyphenyl)2-oxoethyl)phenoxy)acetate ethyl 2-(3-(2-(3-hydroxyphenyl)1-oxoethyl)phenoxy)acetate A mixture of 3,3'-dihydroxydeoxybenzoin (0.05 mol), ethyl bromoacetate (0.05 mol) ad $K_2CO_3$ (0.05 mol) in 50 mL of DMF is stirred at room temperature overnight. The reaction mixture is poured into water and extracted with EtOAc. The organic solution is dried and evaporated to dryness. The crude products are separtated by flash chromatography to give the ethyl 2-(3-(2-(3-hydroxyphenyl)-2-oxoethyl)phenoxy)acetate and the ethyl 2-(3-(2-(3-hydroxyphenyl)-1-oxoethyl)phenoxy)acetate.

B. ethyl 2-(3-(2-(3-(2-quinolinylmethyloxy)phenyl)2-oxoethyl)phenoxy)acetate A mixture of ethyl 2-(3-(2-(3-hydroxyphenyl)2-oxoethyl)phenoxy)acetate (0.01 mol), 2-chloromethylquinoline (0.01 mol), and $K_2CO_3$ (0.01 mol) in 20 mL of DMF are heated at 60° C. overnight. After work-up, the crude product is purified by flash chromatography to give ethyl 2-(3-(2-(3-(2-quinolinylmethyloxy)phenyl)-2-oxoethyl)phenoxy)acetate.

C. ethyl 2-(3-(2-(3-(2-quinolinylmethyloxy)phenyl)-2-hydroxyethyl)phenoxy)acetate The product obtained from Step B (5 mmol) in 50 mL of EtOH is treated with (2 mmol) of $NaBH_4$ at room temperature. After 30 min, the reaction mixture is diluted with water and extracted with EtOAc. The organic solution is dried and evaporated and purified by dry column chromatography to give ethyl 2-(3-(2-(3-(2-quinolinylmethyloxy)phenyl)-2-hydroxyethyl)phenoxy)acetate.

D. ethyl 2-(3-(2-(3-(2-quinolinylmethyloxy)phenyl)-2-(carbethoxyethylthio)ethyl)phenoxy)acetate The product obtained from Step C in 50 mL of $CH_2Cl_2$ is treated with 2 mL of $SOCl_2$. The reaction mixture is stirred at room temperature for 2 hr. and then evaporated to dryness. The crude product thus obtained in 20 mL of CH$_2$Cl$_2$ is treated with ethyl 3-mercaptopropionate and triethylamine (1:1) for 16 hr. at room temperature. After evaporation of solvent, the crude product is purified by flash column chromatography to obtain ethyl 2-(3-(2-(3-(2-quinolinylmethyloxy)phenyl)-2-(carbethoxyethylthio)ethyl)phenoxy)acetate.

E.
2-(3-(2-(3-(2-quinolinylmethyloxy(phenyl)-2-carboxyethylthio)ethyl)phenoxy)acetic acid The product obtained from Step D is hydrolyzed with 1N NaOH solution. Acidification followed by purification gives 2-(3-(2-(3-(2-quinolinylmethyloxy)-phenyl)2-carboxyethylthio)ethyl)phenoxy)acetic acid.

EXAMPLE 14
3-(1-[3-(3-(2-quinolinylmethyloxy)phenoxy)benzyl]-1-(N,N-d-dimethylcarbamylethylthio)thiomethyl)priopionic acid A.
3-[(1-carbomethoxyoxyethylthio-1-N,N-diethylcarbamylethylthio)methyl]benzaldehyde A solution of isophthaldehyde (0.1 mol), N,N-dimethyl 3-mercaptopropionamide (0.1 mol), thiolacetic acid (0.1 mol) and p-tosic acid (0.01 mol) in 100 mL of CH$_2$Cl$_2$ are stirred for 24 hr. The reaction mixture is washed with water, dried and evaporated to dryness. The crude product is purified by flash chromatography. The product thus obtained (0.05 mol) is treated with 0.05 mol of sodium methoxide in the presence of 0.06 mol of methyl acrylate in 50 mL of methanol. After evaporation of solvent, the crude product is purified by flash chromatography to give 3-[(1-carbomethyoxyethylthio-1-N,N-diethylcarbamylethylthio)methyl]benzaldehyde.

B.
3-[(1-carbomethoxyethylthio-1-N,N-dimthylcarbamylethylthio)methyl]benzyl chloride The aldehyde obtained from Step A (0.05 mol) is 100 mL of EtOH is treated with 0.02 mol of NaBH$_4$ at 5° C. for 1 hr. Excess hydride is decomposed with dilute acid followed by extraction with ethyl acetate. The organic solution is dried and evaporated to dryness. The crude product thus obtained is 50 mL of CH$_2$Cl$_2$ is treated wtih thionyl chloride to give 3-[(1-carbomethoxyethylthio-1-N,N-dimthylcarbamylethylthio)methyl]benzyl chloride which is used directly in the next step.

C.
3-(-[3-(3-(2-quinolinylmethyloxy)phenoxy)benzyl]-1-(N,N-dimethylcarbamylethylthio)thioethyl)propionic acid A mixture of 3-(quinolin-2-yl-methloxy)phenol (0.01 mol), the benzyl chloride derivative of Step B (0.01 mol) obtained above and K$_2$CO$_3$ (0.012 mol) in 50 mL of DMF is heated at 50° C. overnight. The reaction mixture is poured into water and extracted with ethyl acetate. After evaporation of solvent, the crude product is purified by flash chromatography. The purified compound is then hydrolyzed with 1.1 equiv of NaOH solution for 2 hr. The reaction mixture is then acidified and extracted into ethyl acetate. The organic solution is dried and evaporated to dryness. Purification by flash chromatography gives 3-(-[3-(3-(2-quinolinylmethyloxy)phenoxy)benzyl]-1-(N,N-dimethylcarbamylethylthio)thioethyl)propionic acid.

When 3-mercaptopropionate in Step D is replaced by the compound of Table VI then the corresponding product is prepared.

Table VI
ethyl 3-mercaptopropionate
methyl 2-mercaptopropionate
methyl 3-mercaptopropionate
methyl 4-mercaptobutyrate
methyl 3-mercaptobutyrate
2-mercapto-N,N-dimethylpropionamide
3-mercapto-N,N-dimethylbutyramide
3-mercapto-N,N-diethylpropionamide When N,N-dimethyl-3-mercaptopropionamide in Step A is replaced by the compounds of Table VII the corresponding product is prepared.

Table VII
N,N-dimethyl-2-mercaptoacetamide
N,N-dimethyl-3-mercaptoacetamide
N,N-diethyl-3-mercaptoacetamide
N,N-dimethyl-4-mercaptobutyramide When thiolacetic acid in Step A is replaced by the compound of Table VIII the corresponding product is obtained.

Table VIII
thioacetic acid
3-thiopropionic acid
4-thiobutyric acid
3-thiobutyric acid
2-thiopropionic acid When the procedure of Example 14 is followed and the starting materials are selected from Tables VI and VII then the corresponding product is obtained.

EXAMPLE 15
methyl 2-(2-((4-(2-quinolinylmethyloxy)-2-carbomethoxybutyl)phenoxymethyl)phenoxy)acetate 2-(2-((4-(2-quinolinylmethyloxy)-2-carboxybutyl)-phenoxymethyl)phenoxy)acetic acid A. ethyl 5-((2,5-dibenzyloxy)phenyl)valerate A solution of 2,4-dibenzyloxybenzaldehyde (0.1 mol) in 30 mL of DMF is added dropwise to a solution of (carbethoxypropyl)triphenyphozphorane (0.11 mol, prepared from (carbethoxypropyl)triphenylphosphonium bromide and sodium hydride) in 100 mL of DMF over a period of 20 min. The reaction mixture is stirred at room temperature overnight and poured into water and extracted with EtOAc. The organic solution is washed well with H$_2$O, dried, and evaporated to dryness. Purification by flash chromatography gives ethyl 5-((2,5-dibenzyloxy)phenyl)valerate.

B. 5-(2,5-dihydroxyphenyl)valeric acid

Ethyl 5-(2,5-dienzyloxy)phenyl)valerate (0.05 mol) in 200 mL of EtOH is hydrogenated with 2 g of 5% Pd/C at 50 psi for 5 h. Filtration and evaporation of solvent gives 5-(2,5-dihydroxyphenyl)valeric acid.

C. ethyl 5-(5-(2-quinolinylmethyloxy)-2-hydroxyphenyl)valerate

A mixture of 2-chloromlethylquinoline (0.03 mol), 0.03 mol of the hydroquinoline derivative obtained from Step B and K$_2$CO$_3$ (0.06 mol) in 50 mL of DMF are heated at 60° C. overnight. The reaction mixture is poured into water, and extracted with EtOAc. The combined organic extracts are washed well with water, dried, and evaporated to dryness. The crude product is purified by flash chromatography to give ethyl 5-(5-(2-quinolinylmethyloxy)-2-hydroxyphenyl)valerate.

D. methyl 2-(2-((4-(2-quinolinylmethyloxy)-2-carbomethoxybutyl)phenoxymethyl)phenoxy)acetate

2-(2-((4-(2-quinolinylmethyloxy)-2-carboxybutyl)phenoxymethyl)phenoxy)acetic acid A mixture of the phenolic compound obtained in Step C (0.01 mol), methyl 2-(chloromethyl)phenoxyacetate (0.01 mol) and K$_2$CO$_3$ (0.011 mol) in 50 mL of DMF is heated at 60° C. overnight. After work-up, the crude product is purified by flash chromatography to give methyl 2-(2-((4-(2-quinolinylmethyloxy)-2-carbomethoxybutyl)phenoxymethyl)phenoxy)acetate. The diester is hydrolyzed with 1 NaOH solution in dioxane, acidified to pH 5 and extracted into EtOAc to give 2-(2-((4-(2-quinolinylmethyloxy)-2-carboxybutyl)phenoxymethyl)phenoxy)acetic acid.

We claim:

1. A compound of the formula

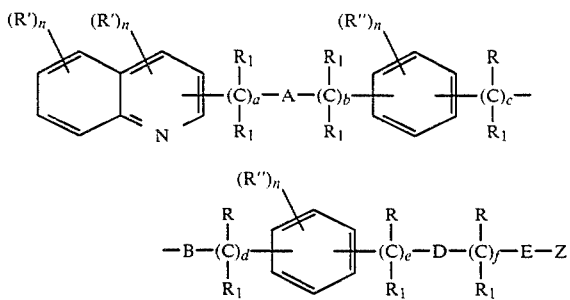

where:
A is O or S;
B is a chemical bond, O, S, SO, SO$_2$, NR$_1$,

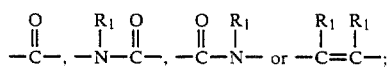

D is O, S, NR$_1$,

or a chemical bond;
E is a chemical bond or

a is 0-2;
b is 0-1;
c is 0-4;
d is 0-5;
e is 0-4;
f is 0-5;
n is 0-2;
R' is independently
  hydrogen,
  alkyl having 1 to 6 carbon atoms,
  hydroxy,
  alkoxy having 1 to 6 carbon atoms,
  carboxy,
  carbalkoxy wherein alkoxy has 1 to 6 carbon atoms,
  halo,
  nitro,
  trifluoromethyl,
  cyano,
  acetyl,
  propionyl or
  benzoyl;
R'' is independently
  hydrogen,
  hydroxy,
  alkoxy having 1 to 6 carbon atoms,
  halo,
  trifluoromethyl,
  —CH$_2$R,
  —CH$_2$—O—(CH$_2$)$_x$—X or
  R;
R$_1$ is independently
  hydrogen,
  alkyl having 1 to 6 carbon atoms,
  benzyl or
  phenethyl;
R is
  —(CH$_2$)$_x$—X,
  —O—(CH$_2$)$_x$—X (when not geminal to A or B when A or B is O);
  —S—(CH$_2$)$_x$—X or
  —NR$_1$—(CH$_2$)$_x$—X where x is 0-3; and
X is
  hydrogen,
  alkyl having 1 to 6 carbon atoms,
  alkenyl having 2 to 6 carbon atoms,
  cycloalkyl having 3 to 6 carbon atoms,
  phenyl,
  benzyl,
  phenethyl,
  hydroxy,
  alkoxy having 1 to 6 carbon atoms,
  aralkoxy wherein aryl is phenyl and alkoxy has 1 to 6 carbon atoms,
  amino,
  mono- and di-alkylamino having 1 to 6 carbon atoms,
  benzylamino,
  phenethylamino,
  acetylamino,
  propionylamino,
  benzoylamino,
  —CONR$_1$R$_1$,
  —COOR,
  —CN,
  tetrazolyl,
  acetylsulfonamido,
  propionylsulfonamido or
  benzoylsulfonamido;
vicinal R groups together may be (CH$_2$)$_y$— where y is 1-4, thus forming a 3-6 membered ring;

geminal $R_1$ and R groups may together form a spiro substituent, —$(CH_2)_z$—, where z is 2 to 5;

geminal $R_1$ or $R_1$ and R groups may together form an alkylidenyl substituent,

Z is —$COOR_1$;
—CN;

where $R_3$ is
hydrogen,
alkyl having 1 to 6 carbon atoms,
trifluoromethyl,
phenyl or
benzyl;

—$OR_1$ or
tetrazolyl or substituted tetrazolyl where the substituent may be alkyl having 1 to 6 carbon atoms,
carboxyalkyl wherein alkyl has 1 to 6 carbon atoms, or
carbalkoxyalkyl wherein alkoxy has 1 to 6 carbon atoms and alkyl has 1 to 6 carbon atoms; and
pharmaceutically acceptable salts thereof.

2. A compound of claim 1 of the formula

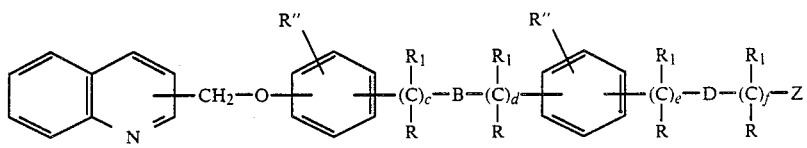

where one of R is —$(CH_2)_x$—X; —S—$(CH_2)_x$—X; —O—$(CH_2)_x$—X; (when not geminal to A or B when A or B is O); or —$NR_1$—$(CH_2)_x$—X; and/or one of R'' is —$CH_2R$; R or —$CH_2$—O—$(CH_2)_x$—X and X is —$CONR_1R_1$, —$COOR_1$, —CN, tetrazolyl or acylsulfonamido.

3. A compound of claim 2 where B is O, S,

or a chemical bond; Z is —$COOR_1$ —$CON(R_1)_2$ or tetrazolyl.

4. A compound of claim 3 of the formula

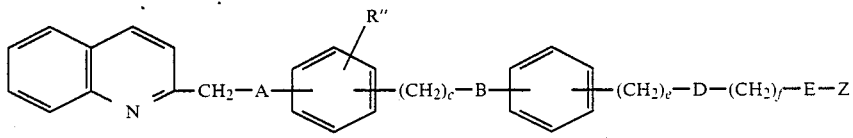

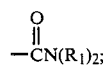

5. A compound of claim 3 of the formula

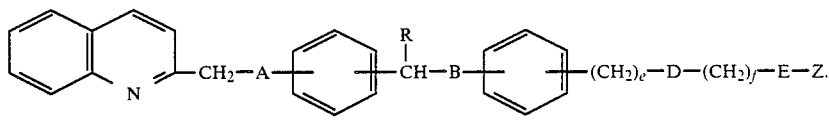

6. A compound of claim 3 of the formula

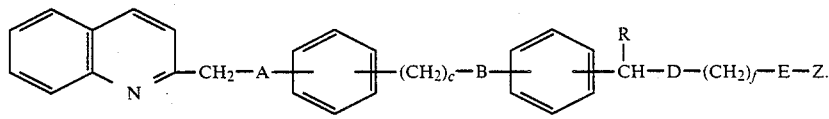

7. A compound of claim 3 of the formula

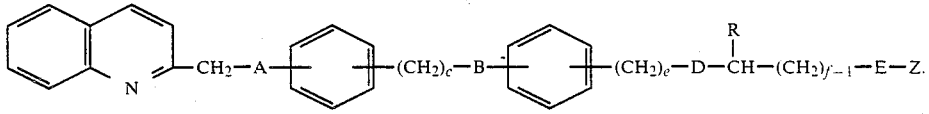

8. A compound of claim 3 of the formula

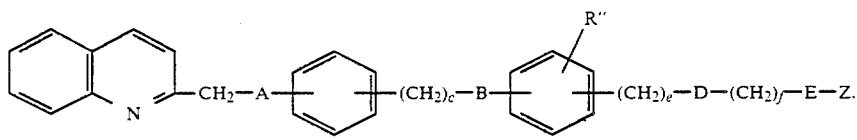

9. A compound of claim 3 of the formula

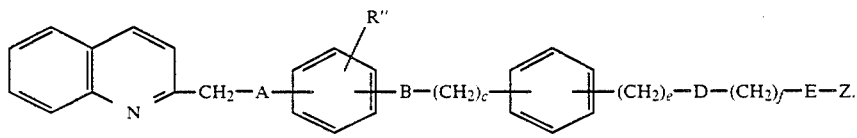

10. A compound of claim 3 of the formula

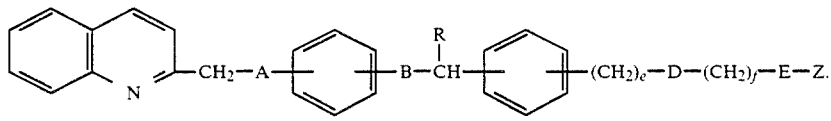

11. A compound of claim 3 of the formula

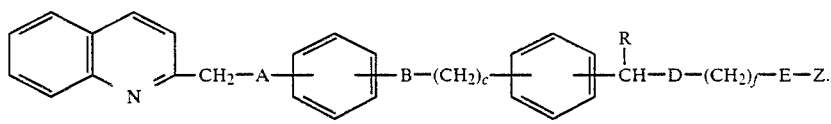

12. A compound of claim 3 of the formula

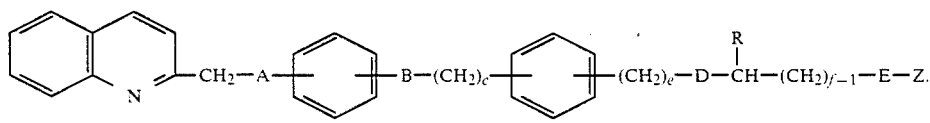

13. A compound of claim 3 of the formula

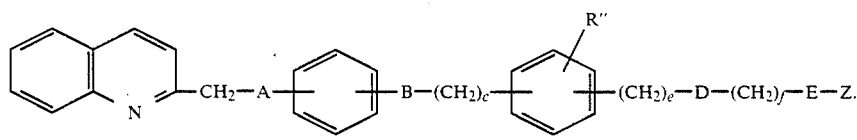

14. A compound according to claim 1 which is 2-hydroxy-3-((2-carboxyethyl)thio-3-[(2-(4-((quinolin-2-yl)methyloxy)phenoxymethyl)phenyl]propionic acid.

15. A compound according to claim 12 which is 4-(2-(4-((quinolin-2-yl)metholoxy)phenoxymethyl)phenoxy)-4-carboxybutyric acid.

16. A compound according to claim 11 which is 3-(-1-[3-(3-(2-quinolinylmethyloxy)phenoxy)benzyl]-1-(N,N-dimethylcarbamylethylthio)thiomethyl)propionic acid.

17. A compound according to claim 1 which is 2-(3-(3-(quinolin-2-yl)methyloxy)phenoxymethyl)phenoxy)-valeric acid.

18. A method for the treatment of hypersensitive ailments in a patient requiring such treatment which comprises administering to such patient an effective amount of a compound of the formula according to claim 1.

19. A pharmaceutical composition for the treatment of hypersensitive ailments in a patient requiring such treatment comprising an effective amount of a compound according to claim 1 in admixture with a pharmaceutical carrier.

* * * * *

UNITED STATES PATENT AND TRADEMARK OFFICE
CERTIFICATE OF CORRECTION

PATENT NO. : 4,920,131
DATED : April 24, 1990
INVENTOR(S) : Huang et al.

It is certified that error appears in the above—identified patent and that said Letters Patent is hereby corrected as shown below:

On the title page:

The Notice information which appears on the title page of the above-reference patent is not applicable. Please delete the following:

[*] Notice: The portion of the term of this patent subsequent to April 24, 2004 has been disclaimed.

Signed and Sealed this

Nineteenth Day of April, 1994

Attest:

BRUCE LEHMAN

*Attesting Officer*  *Commissioner of Patents and Trademarks*